United States Patent [19]
Ingram et al.

[11] Patent Number: 5,432,322
[45] Date of Patent: Jul. 11, 1995

[54] ELECTRIC HEATING PAD

[75] Inventors: Aaron N. Ingram, Canton; Richard A. Wise, Marietta, both of Ga.; John W. Carroll, Winston-Salem, N.C.; Thomas C. Himes, Conyers, Ga.

[73] Assignee: Bruder Healthcare Company, Marietta, Ga.

[21] Appl. No.: 974,744

[22] Filed: Nov. 13, 1992
(Under 37 CFR 1.47)

[51] Int. Cl.⁶ .................................................. H05B 3/36
[52] U.S. Cl. ............................................................ 219/528
[58] Field of Search .................. 219/212, 528, 543, 544, 219/548, 549, 492, 517; 338/211, 212; 177/134

[56] References Cited

U.S. PATENT DOCUMENTS

| | | | |
|---|---|---|---|
| 1,960,120 | 5/1934 | Möhring | 264/27 |
| 2,122,650 | 7/1938 | Keene . | |
| 2,154,184 | 4/1939 | Roberts . | |
| 2,715,674 | 8/1955 | Abbott et al. | 219/212 |
| 2,745,942 | 5/1956 | Cohen | 219/528 |
| 2,795,680 | 6/1957 | Peck | 201/63 |
| 2,936,360 | 5/1960 | Suarez | 219/528 |
| 3,130,289 | 4/1964 | Katzman et al. | 219/528 |
| 3,547,725 | 12/1970 | Shomphe et al. | 219/528 |
| 3,668,367 | 6/1972 | Williams | 219/212 |
| 3,996,447 | 12/1976 | Bouffard et al. | 219/541 |
| 4,139,763 | 2/1979 | McMullan et al. | 219/528 |
| 4,149,066 | 4/1979 | Niibe | 219/505 |
| 4,210,216 | 7/1980 | Godden | 177/134 |
| 4,429,215 | 1/1984 | Sakai et al. | 219/528 |
| 4,429,216 | 1/1984 | Brigham | 219/528 |
| 4,450,496 | 1/1984 | Doljack et al. | 219/212 |
| 4,485,297 | 11/1984 | Grise | 219/528 |
| 4,523,085 | 6/1985 | Grise | 219/528 |
| 4,542,285 | 9/1985 | Grise | 219/543 |
| 4,574,186 | 3/1986 | Sakai et al. | 219/528 |
| 4,626,664 | 12/1986 | Grise | 219/525 |
| 4,633,068 | 12/1986 | Grise | 219/211 |
| 4,656,339 | 4/1987 | Grise . | |
| 4,659,905 | 4/1987 | Gabrosek et al. | 219/212 |
| 4,690,347 | 9/1987 | Grise | 242/57.1 |
| 4,717,812 | 1/1988 | Makita | 219/528 |
| 4,746,838 | 5/1988 | Kay | 313/519 |
| 4,749,844 | 6/1988 | Grise | 219/541 |
| 4,774,397 | 9/1988 | Grise | 219/549 |
| 4,788,417 | 11/1988 | Gratlind | 219/528 |
| 4,814,586 | 3/1989 | Grise | 219/549 |

Primary Examiner—Geoffrey S. Evans
Attorney, Agent, or Firm—Needle & Rosenberg

[57] ABSTRACT

The improved heating pad includes a flexible, thin film heating element with two independent semiconductor circuits printed on an electrically insulating surface, laminated between overlying and underlying organic polyester sheets, and electrically connected to an external power source, wherein the heating element is hermetically sealed in an outer organic polymer covering. Thermostats are positioned directly over the semiconductive circuit traces. The circuit traces are connected in parallel by a multi-position switch, with each circuit capable of being energized separately or in combination, and each circuit capable of providing heat over the entire area of the pad. A circuit protective device provides a varistor across the power supply and a fast-acting fuse in series with the circuit traces.

25 Claims, 6 Drawing Sheets

ELECTRIC HEATING PAD

BACKGROUND OF THE INVENTION

1. Field of the Invention

This invention relates generally to electrically heated panels. In particular, this invention is an electric thin film heating element combined with its enclosure into a single entity heating panel providing excellent drapeability and conformance to body contour, more even temperature distribution, and increased safety.

BACKGROUND

Heating elements of the sort used in therapeutic heating pads have been known in the art for some time. However, these pads often are bulky, offer inconsistent heating surfaces, and present potential fire and electric shock hazards. In U.S. Pat. No. Re. 29,641, the invention provides a resistance wire heating pad pliable in all directions and generally able to fit the contours of parts of the body. Despite its improvement over the prior art, that heating pad still utilized a single wire clement, necessarily bulky and limiting the flexibility of the produced heating element. Furthermore, in order to generate and withstand the proper amount of heat, the wires used in those kinds of devices were characteristically thick and often coated with an insulating layer to prevent shock and shorting hazards. Often, the changeover from the more rigid and stiff heating pads, such as the one in U.S. Pat. No. 2,154,184, created dangerous temperature lags since the new pads would substantially overshoot their target temperatures before relaxing to the desired steady-state temperature. Misshaping of the clement configuration during flexing of the pad and the uneven, temporal nature of heating with single wire elements caused these problems. U.S. Pat. No. 3,889,100 improved the target temperature overshooting problem by more strategic location of the thermostats and a backward/forward sinuous looping of the heating element to allow more accurate temperature gauging while retaining adequate flexibility of the pad. That construction, however, still utilized a single wire heating element enclosed and sewn or heat staked into a loose fabric covering (which was often flammable).

A major innovation in heating pad design was the creation of thin resistive elements which were thinner and more flexible than the single wire constructions previously discussed. U.S. Pat. Nos. 2,795,680 and 4,814,586 disclose a method for creating thin printed resistors. These resistors are formed by an adherent resistance layer made of an epoxy resin binder containing conductive material. This binding material is deposited onto a substrate. After the epoxy fixes, the residue results in a printed resistor. Like single wire heating elements, when current is subsequently passed through these resistors, they heat. Printed resistors have been successfully incorporated into flexable heating panels. See, e.g., U.S. Pat. Nos. 4,149,066 and 4,429,216.

Furthermore, both printed resistor heating elements and the previously discussed single wire type heating elements may be arrayed into heating pads with multiple elements. In these configurations, energizing different combinations of the heating elements results in differing degrees of heat. See U.S. Pat. No. 2,122,650. In addition, the thin films may be energized in parallel as disclosed in U.S. Pat. Nos. 4,485,297 and 4,452,285. In U.S. Patent No. 3,668,367, two heating elements of differing lengths are connected to a multi-position switch so they could be energized in series, parallel, or selectively one at a time. The arrangement, however, does not provide for different temperatures to be selected over the entire heating pad. Instead, the invention allowed different areas of the pad to be heated selectively. Thus, the temperature possibilities arising from the multiple settings did not provide for uniform temperature distribution over the entire pad for each temperature setting. The same disuniformity is the intentional result of U.S. Pat. No. 4,659,905 concerning an electric blanket directed toward arthritic persons so that the 'head' and 'foot' areas may be separately energized.

Many commercial heating pads today consist of a heating element loosely encased in a packaging envelope. Often, the heating element is insulated in highly flammable material. Furthermore, the resulting pockets of air decrease the efficiency of heat transfer from the pad to the object it is draped over. Separation of the heating element from the enclosure increases the bulkiness of the heating pad. Therefore, these pads are not very drapeable.

SUMMARY OF THE INVENTION

The subject of this invention presents several advantages over the prior art. The heating element and its enclosure combine to form a single, pliable, thin unit, making it more able to conform to the body of the user than previous heating pads.

This invention eliminates the need for a thick single wire heating element which is wound in several patterns and secured by sewing or heat staking. Such devices presented the danger of the heating element breaching the protective covering. Also, movement of the heating element inside the covering could lead to nonuniform heat distribution and dangerous local temperature spots.

In one preferred embodiment of this invention, the thin film conductor is enclosed directly into a foamed polyvinyl chloride (PVC) shell which eliminates both of these hazards. First, it is impossible for the heating element to breach the PVC enclosure since it is not a wire, but a thin, flexible band of semiconductor material. Next, since the conductive film is deposited permanently within and onto the PVC foam encasing, movement within the heating pad of the heating element is impossible. Therefore, the single unit pad described by this invention is much safer and efficient than the prior art.

Alternatively, the heating element of the present invention can be overmolded, fully encapsulated into a material such as polyurethane, PVC, or another suitable material by RIM molding, low pressure injection molding or casting. The process of overmolding creates a heating element and enclosure which functions on a single entity with excellent drapeability and conformance to body contour. Selection of weighted materials allow for further improvements in drape. Temperature is more evenly distributed due to the absence of air pockets and the direct contact of the element with the outer covering material. This process also eliminates the more flammable components of traditional vinyl envelopes.

Prior art heating pads have the intrinsic characteristic of significantly overshooting their steady state operating temperature. U.L. 130 standard recognizes this by providing for an initial overshoot temperature of 194 deg F. and subsequently steady state operating temperature max of 176 deg F. Prior art heating pads in a high heat setting typically overshoot in the range of 180 deg F. and operate at 150 deg F. max, with many averaging in the 145 deg F. range. The placement of the thermostat in this invention provides for direct contact with the heating element surface. This design characteristic allows for significantly lower initial overshoot temperatures 165 deg F. to 170 deg F. being typical with operating temperatures in the 150 deg F. range. The thinner profile provides for less thermal mass and the unit is inherently more responsive to changes in the heat transfer occurring at its surface. The unit shows significantly improved heat profiles relative to prior art technology which frequently exhibits temperature gradients across the surface of 30 deg F. or more.

Heat is provided by two completely isolated heating circuits, using dielectric insulators and strategically placed die cuts and mastics. These circuits can be energized independently or together to produce low, medium, or high temperature settings. Each circuit provides heat to the entire surface area of the panel.

The device of this invention also includes other safety features not present in previous heating devices. The common wall circuit which provides the power for many everyday products generally will not open until a very dangerous hazard for the user has already arisen. Since the conductive traces of each heating circuit of this invention are arrayed in parallel, failure of one of the individual parallel conductive traces will not render the unit inoperative. The heating elements work under the premise of parallel resistances. Each trace is working independently of the others in the element. If the integrity of a single trace is comprised, the current continues to flow through the others, but the total current draw from the entire unit is reduced. Each trace acts as a current limited device in that they will form an open circuit at current input of more than 0.65 amps to the entire element. Laws of parallel resistance elements predict a reduced current draw to the system.

In addition, failure of one of the traces of this invention will not create dangerous voltage levels throughout the unit because the unit contains a protective circuit designed to remedy the problem of over current from a wall circuit. This circuit, a fast-acting 0.5 amp fuse and a varistor, is an intrinsic part of the power switch on the device's power cord. The fuse is normally non-resettable.

The heating panel of the present invention has many uses, including, but not limited to, therapeutic moist and dry heating pads, moist and dry heat therapy products for the professional and sports trade, hospital therapeutic heating pads, foot and bed warmers, arthritic therapeutic products such as gloves, wraps, etc., sinus heat therapy products.

DETAILED DESCRIPTION OF THE PREFERRED EMBODIMENTS

Figure 1:
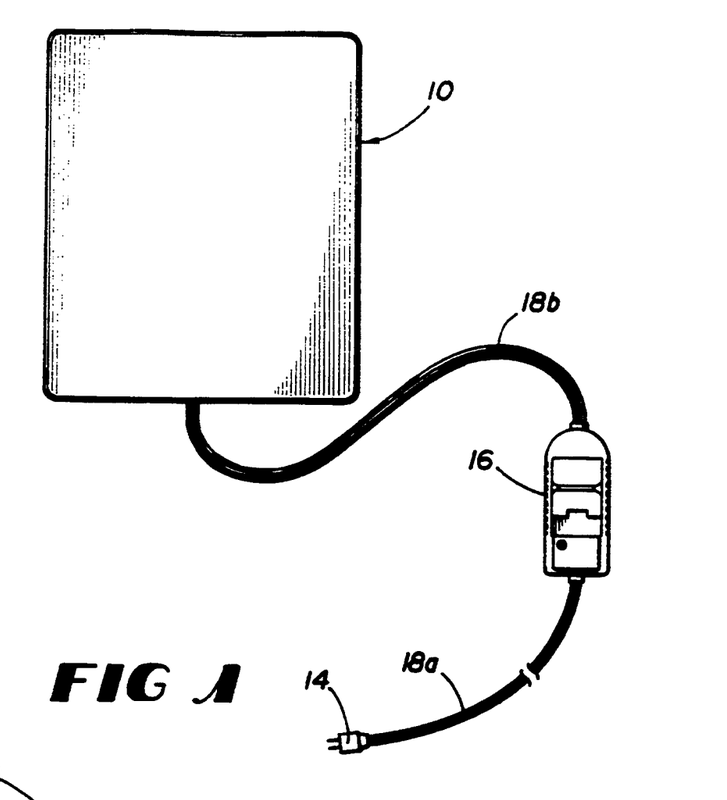
FIG. 1 is a view of one embodiment of the present invention.
Figure 2:
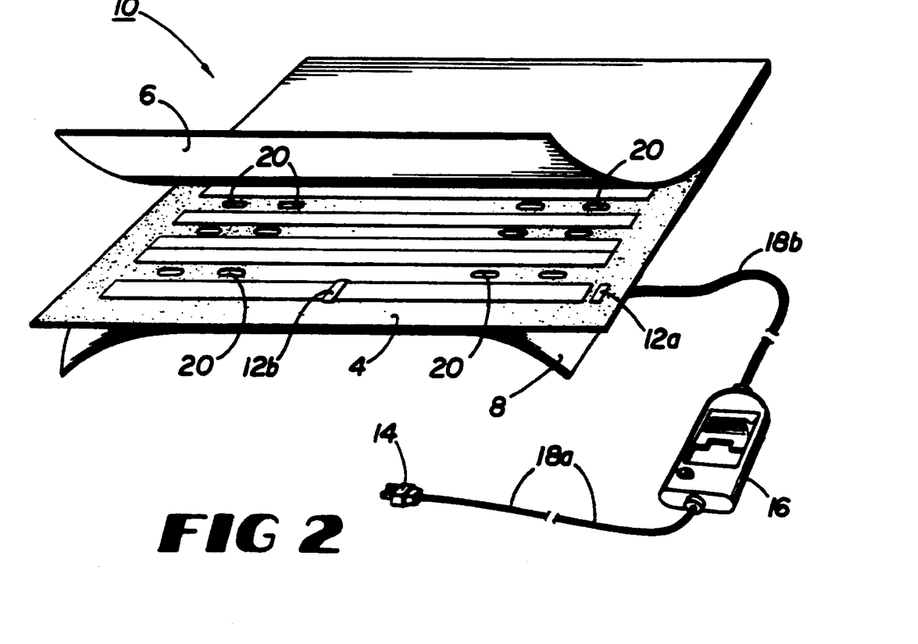
FIG. 2 is an open-ended view of the heating pad showing the heating element, thermostats, outer organic polymer covering, cord set and switch.
Figure 3:
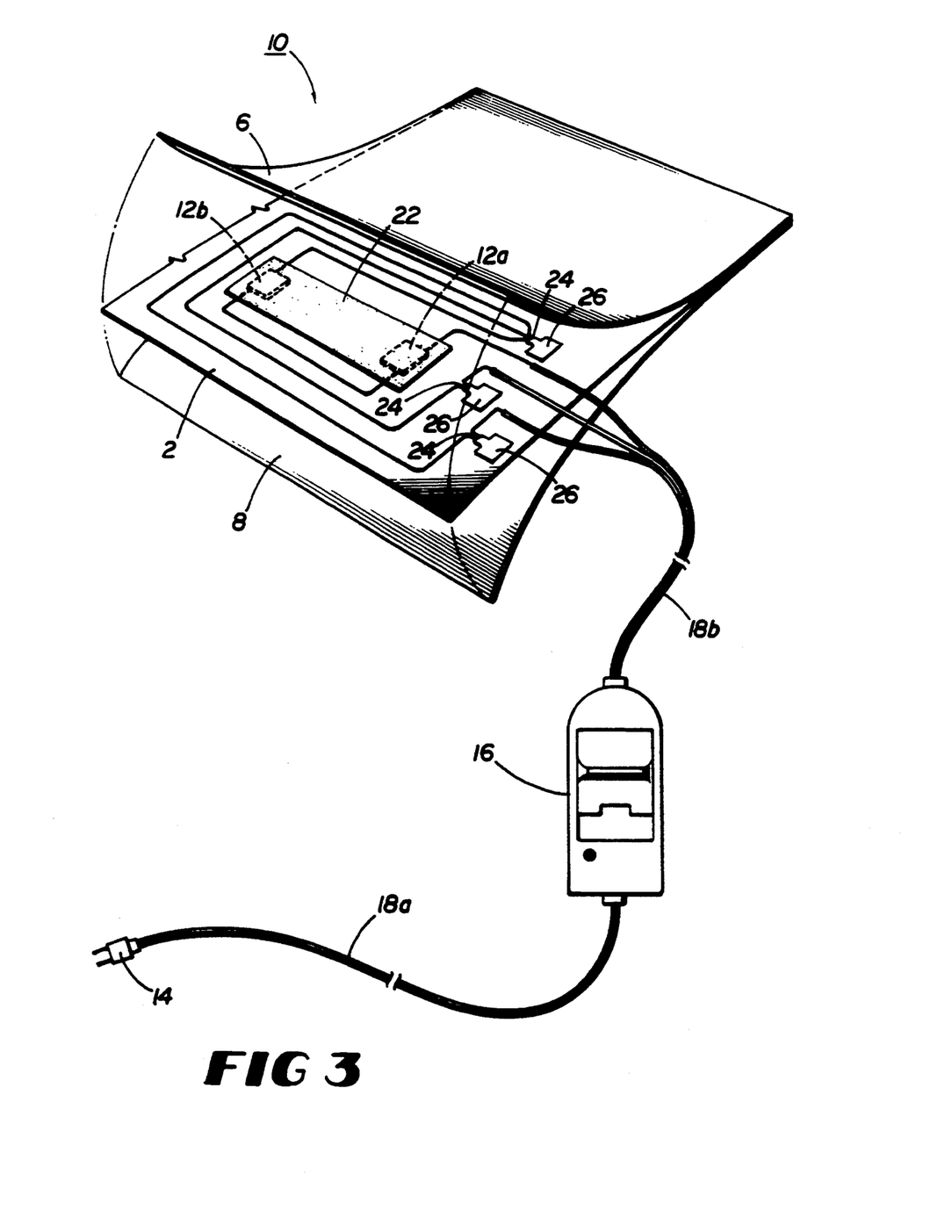
FIG. 3 is an open-ended view of the heating pad showing the thermostat location and attachment of the cord set.

FIGS. 1 through 3 show the heating pad generally designated 10, and the cord set 14, 18a and 18b and switch assembly 16. In one preferred embodiment the overall dimensions of the heating pad 10 are about 12" wide by 14" long by ⅛" thick.

Figure 7:
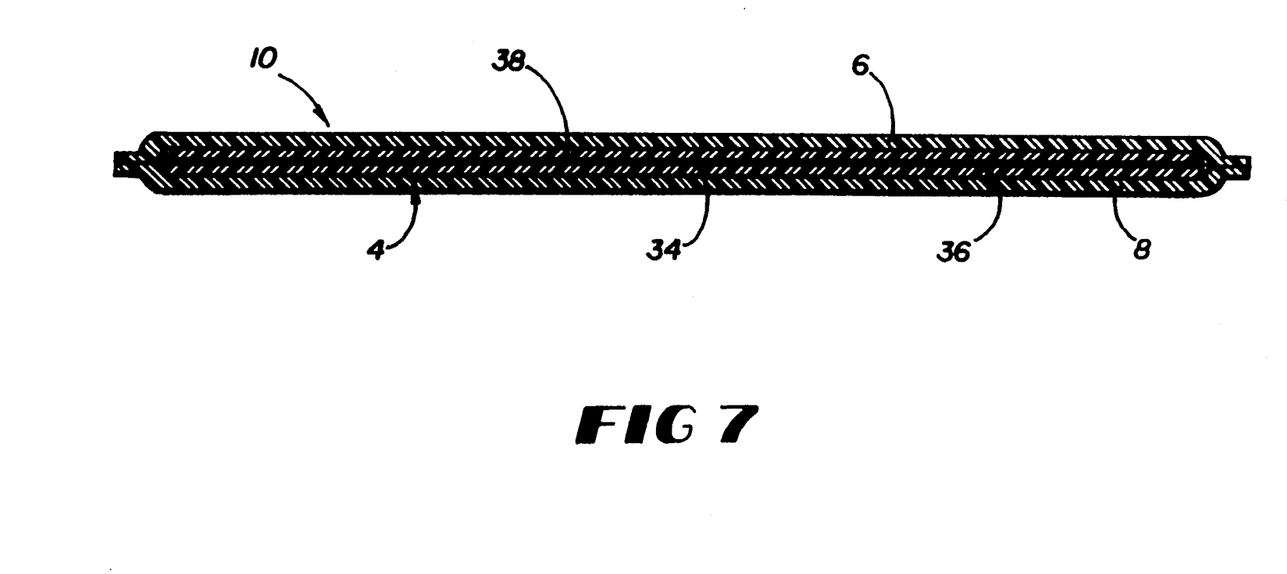
FIG. 7 is a cross-sectional view of the heating pad.

The heating element 4 is a layered construction of four different components (bottom Mylar substrate 34, middle heat-cured screened resistive pattern, conductive tape, outer Mylar sheets 36, 38 as shown in FIG. 7) irreversibly fused into a single unit. Such thin film printed resistor elements are commercially available. A preferred embodiment of this invention utilizes the Flexwatt Corporation CHE-109H 20 element (Flexwatt Corporation, Canton, Mass.). The Flexwatt heating element utilizes two parallel heating circuit traces 2, one of about 370Ω and the other of about 497Ω. Both circuits are designed to provide heat throughout the entire surface of the pad. The approximate total thickness for the four component sealed heating element 4 is 0.007".

Figure 4:
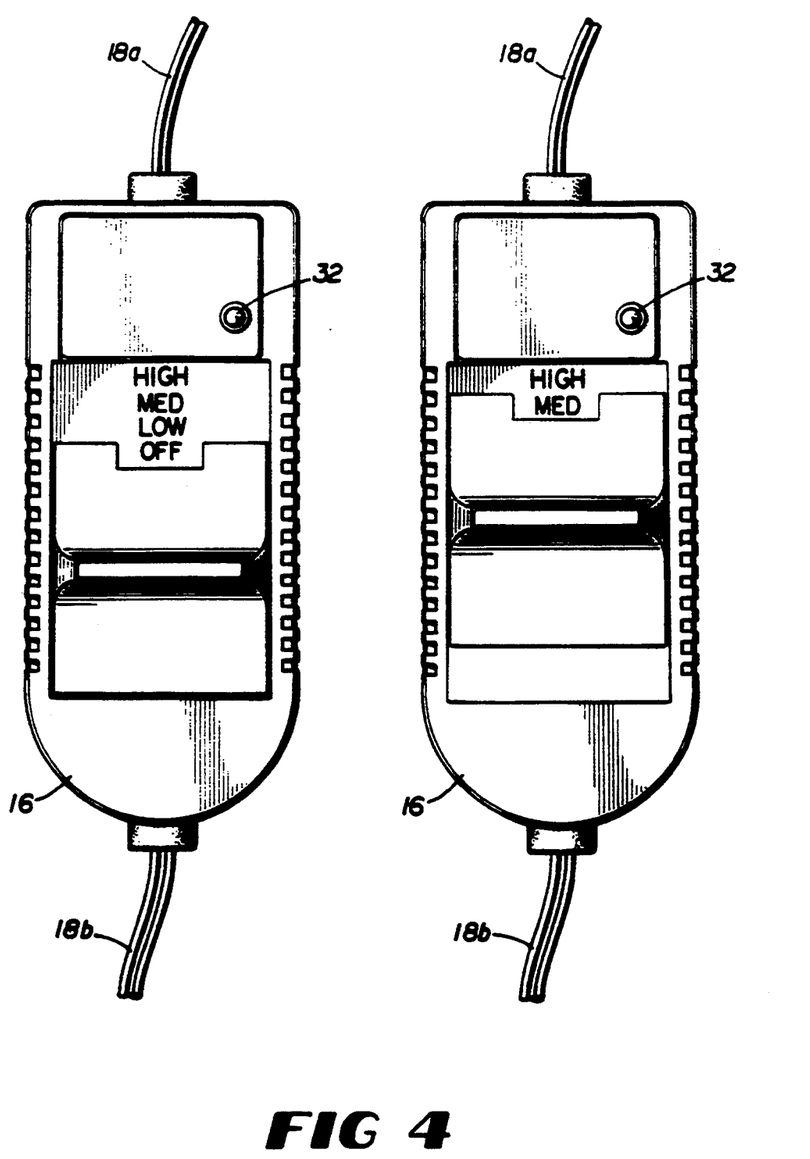
FIGS. 4 and 5 show the multi-position switch, circuit configuration and circuit protective devices.
Figure 5:
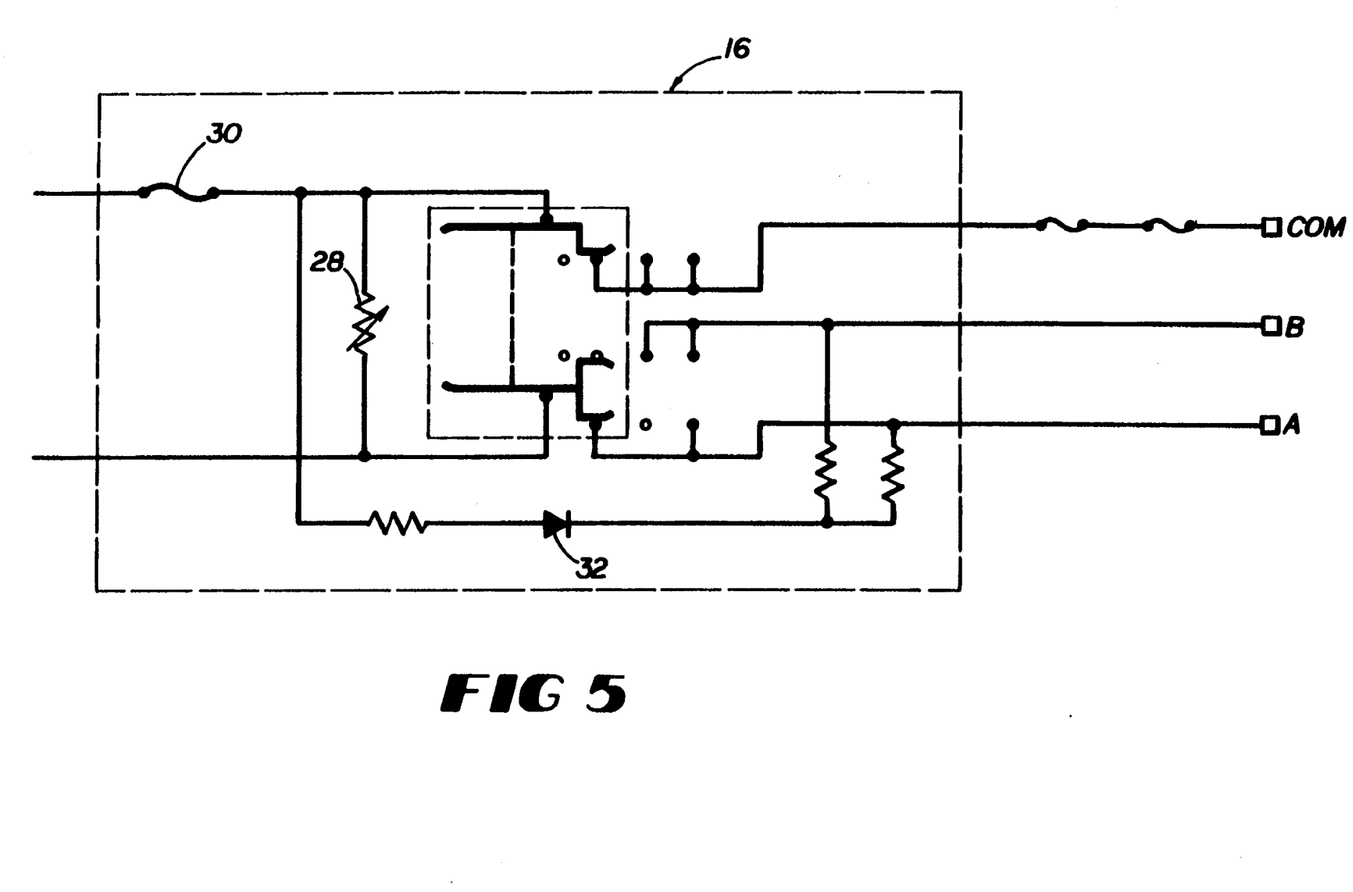

Referring to FIGS. 2, 4 and 5, the two separate heating circuits of the screened heating element 4 are utilized in this invention to achieve 'Low', 'Medium', and 'High' settings controlled by a four-position switch 16. The first heating circuit or 'A' connection ('Low' switch position) is about a 497Ω circuit and achieves an open air condition temperature of about 122°-125° F. The second heating circuit or 'B' connection ('Medium' switch position) is about a 370Ω circuit and achieves an open air condition temperature of about 135°-137° F. The 'High' switch position uses both the 'Low' and 'Medium' switch positions in parallel to achieve the 'High' heat. This combination heating circuit achieves an open air condition temperature of about 152°-157° F.

The first phase of construction schematically shown in FIG. 2, involves cutting the stress relieving slots 20 into the polyester (Mylar) laminate of the heating element. A commercial die cutting machine is used to precision cut the 1/16 inch by ½ inch slots in clear areas of the laminated element between semiconductor traces. Two parallel rows of 6 slots 20, are located at approximately 1½ inches and 3 inches, respectively, from each edge of the pad. This slot configuration increases flexibility and reduces stress on the circuit traces of the pad. It is contemplated that other slot sizes and configurations can also be utilized to achieve the desired flexibility.

The second phase of the construction shown in FIGS. 2 and 3 involves connecting the polyester (Mylar) sealed heating element 4 to the switch and power supply. An approximately 1-inch square die cut is made through the circuit connecting conductive tapes, located along the lateral edges of the element and overlaying the ends of the conductive traces. Film-piercing brass contacts (Winuation Industries of Hong Kong) are placed over and under the polyester and conductive tape of the element in a 'V' fashion at the die cut edges and each contact's crimp tip for 18-AWG wire is pressed flat with a crimping tool. This crimping pierces the polyester film and conductive tape to form a conductive termination 24.

Electrical wires 18b comprising the cord set are attached (soldered) to the terminations of the heating element and are further retained using hot melt adhesive (3-M, Jetmelt 3789-PG) which is flexible at the termination points 26 and has a high activation point of about 280° F. The cord set (Wination Industries, Ltd., Hong Kong) is a standard 125 Volt unit, with a two prong, polarized, non-grounded attachment plug on the line end of the cord-set. The plug 14 is molded into the cord. The flexible cord is Type SPT-2, 18/2 18a & 18/3 18b, with an ampacity rating of 6 amperes. The maximum current rating of the heating element is 1.5 amperes. The cord-set is about 72 inches from pad entry to plug tip.

The thermostats, 12a, 12b in FIGS. 2 and 3, (Canthern model V11 70-2-5, Montreal, Quebec) are bi-metallic snap action design normally closed with a ±5° C. tolerance set at 70° C. The thermostats are arrayed in series as designated in FIGS. 3 and 6. Thermostat 'A' 12a is located at the lower end of the heating pad 10 closest to the power supply approximately 2 inches from the power supply. Thermostat 'B' 12b is located centrally in the heating pad approximately 6 inches away from the power supply. A standard thermal grease is applied between the interface of the thermostats 12a, 12b and the outer polyester sheet of the heating element. Both thermostats 12a, 12b are positioned directly over the heat traces which reduces the initial overshoot temperature to approximately 82° C. After the thermostats 12a, 12b are placed, a layer of 2" mastic electrical tape (3-M #06147) is applied to the bottom of the pad in the contact areas 26. The top of the contact area 26 is sealed with another mastic patch. This also seals the terminations 24 against moisture ingress. A layer of electrical tape 22 2 inches wide×9 inches long is also applied over the thermostats for anti-piercing.

In one embodiment of the invention, FIGS. 2 and 3, the outer organic polymer covers 6, 8 of the pad consist of two sheets of about 1/16 inches thick, foamed polyvinyl chloride (PVC) (L-91-22, Adchem Corp., Westbury, N.Y.). One sheet of PVC is used per cover 6, 8. The foamed PVC overlaps the Mylar substrate of the heating element 4 by about 3/16 inch to ¼ inch on all sides. The PVC foam comes with a 2 mil coating of pressure sensitive adhesive. The adhesive is high temperature (approximately 280° F.) and salt water resistant, thereby providing increased safety and durability. The upper and lower PVC foam sheets are set by a roller press which applies pressure tangentially as the heating element and polymer sheets are fed through the press. The pressure applied to seal the adhesive is between about 10–60 psi.

The edges of the pad are heat sealed in a die cut press. The cutting edge of the die heats to a temperature between 300–350° F. and cuts and seals the edges of the pad on contact. The contact time is adjusted between 0.5 and 5 seconds depending upon the specific organic polymer utilized. The edges of the pad can also be sealed using a solvent exposure or pressure sealing process.

Once the outer polymer covering 6, 8 is laminated to the surface of the element 4 and the edges sealed, the heating pad 10 becomes a single entity. The single entity heating pad 10 of this invention has increased flexibility and drapeability, is less flammable, and provides more uniform heat distribution over the entire surface of the pad than prior art heating pads.

In another embodiment of the present invention, the heating element can be covered by a continuous layer of outer organic polymer by molding the polymer over the element. A mold is fabricated using CIBA-Geigy REN shape material, a composite tooling material. After the mold is fabricated, the heating element 4 with thermostats 12a, 12b and cord set attached, is placed in the mold and clamped shut. A casting type polyurethane (CIBA-Geigy REN:Co: Thane No. TDT-178-34) is then pumped into the mold to fully encapsulate the unit. The cast polyurethane is allowed to heat cure in the mold for 6 to 8 hours. Heat cure is accomplished by turning on the heating pad to the lowest setting and allowing the element to heat the cast polyurethane from inside the unit itself. The mold is unclamped after cure and the finished overmolded, hermetically sealed heating pad is removed. By hermetically sealed is meant a generally air-tight seal around the heating element 10.

Figure 6:
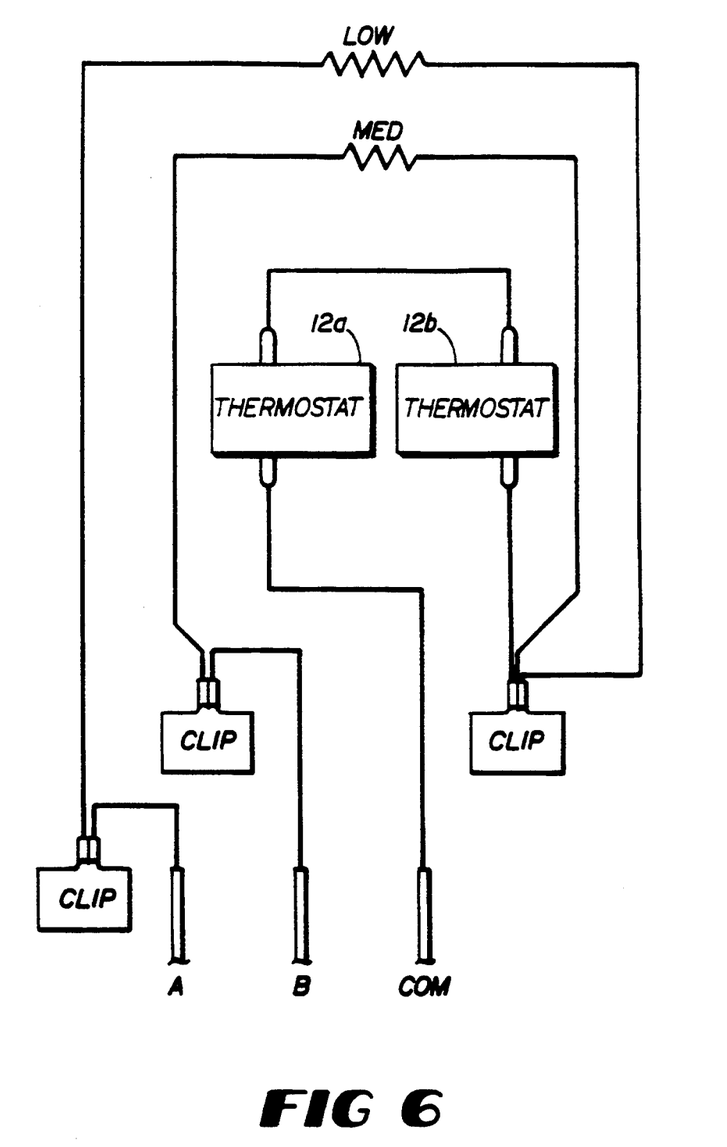
FIG. 6 shows the configuration of the thermostats in the circuit.

Referring to FIGS. 4, 5 and 6, the switch 16 is a single-pole, four position switch (Wination Industries of Hong Kong) used to switch loads from line to line. One conductor of the line is fed through the switch directly to the common point of the element's heating circuits. The other conductor of the line is fed to the pole of the switch. Positions 'A' and 'B' of the switch FIG. 5 correspond to the lower and higher resistive heating circuits of the heating element, respectively. Position 'Com' of the switch connects both the 'A' and 'B' terminals together in parallel for the highest heat output setting. The 'Off' switch position disengages both sides of the line as an added safety feature.

A neon lamp 32 FIGS. 2 and 4, is used to indicate that the heating element 4 is energized. The lamp circuit provides a high resistance in parallel to the heating element 4, thereby having a negligible effect on the power output of the heating element. The lamp circuit dissipates less than ¼ watt of power.

Referring to FIGS. 4 and 5. In another preferred embodiment, the switch 16 contains a circuit protective device comprising a varistor 28, (7 mm MOV Z130-LAZ CKE, Inc., Lucernemines, Penna.) across the power supply to protect against voltage spikes. The varistor increases conductivity as increased voltage is applied, thereby by forming a bypass circuit to protect the switch 16 and heating element 4. A fast-acting 0.5 amp fuse 30 (Bussman 0.5 amp, PCB, Marietta, Ga.) is incorporated into the circuit to prevent current in excess of 0.55 amps from reaching the heating element 4. This circuit can be configured as a single-use unit, a self-resetting unit, or a user-serviceable unit, depending upon selection of the primary component. The preferred configuration is a single use, non-user-serviceable design. This prevents reuse of a device damaged by excessive current flow and is therefore safer. This circuit protective device can be used in a variety of electrical products where consumer protection is an important aspect of the product design, including but not limited to, warming trays and plates chair warmers and heat massage units.

What is claimed is:

1. An electric heating pad comprising:
   a. a flexible heating element, comprising two independent thin film semiconductor circuits printed on an electrically insulating surface and laminated between overlying and underlying organic polyester sheets;
   b. means for electrically connecting said heating element to an external power source;
   c. two outer organic polymer sheets, one sheet disposed on each side of the heating element, with the outer edges of the polymer sheets in contact with each other; and d. means to seal the outer edges of the polymer sheets together to hermetically seal the heating element therebetween.

2. The heating pad of claim 1, and further comprising two thermostats, each one positioned directly over one of the traces of the two independent thin film semiconductor circuits, in a configuration to significantly reduce the initial overshoot temperature of the heating pad.

3. The heating pad of claim 2, and further comprising a thermally conductive grease applied between each thermostat and one of the polyester sheets overlying the traces of the two independent thin film semiconductor circuits to improve thermal conductivity.

4. The heating pad of claim 2, and in which a first one of the two thermostats is located approximately 2 inches from the termination of the connection to the external power source, and a second one of the two thermostats is located approximately 6 inches from the termination of the connection to the external power source and at least 4 inches from the first thermostat.

5. The heating pad of claim 2, and in which the thermostats are held in place by a layer of mastic tape overlying the thermostats forming a tight seal to the outer organic polymer covers of the heating element.

6. The heating pad of claim 1, wherein said independent semiconductor circuits are connected in parallel by a multi-position switch, wherein each circuit is capable of being energized separately or in combination and each circuit is capable of providing heat over the entire area of the pad.

7. The heating pad of claim 6, further comprising a circuit protective device located in the multi-position switch in the circuit for connecting said heating element to an external power source comprising:
  a. a varistor in parallel with the multiposition switch and circuit traces to prevent damage to the unit from voltage spikes and;
  b. a fast-acting fuse in series with the circuit traces.

8. The electric heating pad of claim 7, and further in which the fast-acting fuse acts to electrically disconnect the heating element from the external power source when the current applied to the circuit exceeds about 0.55 amps.

9. The electric heating pad of claim 1, further comprising a flexable hot melt adhesive glue applied over the connections to the external power source, providing a means to further stabilize and retain said electrical connections by directly adhering said electrical connections to the laminated polyester surface of the heating element.

10. The electric heating pad of claim 9, wherein a layer of mastic tape is placed over said glue and terminal connections whereby the mastic tape overlaps said glue and terminal connections and forms a tight seal to the outer polyester layer of the heating element.

11. The electric heating pad of claim 1, further comprising stress relieving slots cut into the polyester laminate of the element in areas between the semiconductor circuit traces.

12. The electric heating pad of claim 11, wherein said stress relieving slots are approximately 1/16 inch by ½ inch.

13. The electric heating pad of claim 11, wherein said stress relieving slots are configured in 2 parallel rows of 6 slots each row located approximately 1½ and 3 inches respectively from the outer edges of the heating element at each corner of the heating element.

14. The heating pad of claim 1, wherein said outer organic polymer covering comprises an upper and lower layer of foamed organic polymer, sealed to the outer surfaces of the heating element with a suitable pressure-sensitive adhesive, the outer coveting being of sufficient size to overlap the heating element on all sides and sufficiently thin to be flexstyle, wherein the foamed organic polymer layers are pressure laminated to the upper and lower surface of the heating element and are sealed along the outer edges of the heating pad.

15. The heating pad of claim 14, wherein the pad is about 12 inches wide by about 14 inches long by about ⅛ inch thick.

16. The heating pad of claim 14, wherein the upper and lower layers of foamed organic polymer have a closed cell design.

17. The heating pad of claim 14, wherein the organic polymer comprises polyvinylchloride.

18. The heating pad of claim 14, wherein the organic polymer comprises polyethylene.

19. The heating pad of claim 14, wherein the organic polymer comprise polyurethane.

20. The heating pad of claim 1, wherein the outer organic polymer coveting comprises a continuous layer of organic polymer molded over the heating element.

21. The heating pad of claim 20, wherein the organic polymer is molded over the heating element by casting said organic polymer around the heating element utilizing a preformed mold.

22. The heating pad of claim 20, wherein the organic polymer is cast to a uniform thickness of about ⅛ inch over all surfaces of the heating element.

23. The heating pad of claim 20, wherein the organic polymer comprises polyurethane.

24. The heating pad of claim 20, wherein the organic polymer comprises polyethylene.

25. The heating pad of claim 20, wherein the organic polymer comprises polyvinylchloride.

* * * * *